(12) United States Patent
Franz et al.

(10) Patent No.: US 8,551,976 B2
(45) Date of Patent: Oct. 8, 2013

(54) PROCHELATORS FOR INHIBITING METAL-PROMOTED OXIDATIVE STRESS

(75) Inventors: Katherine J. Franz, Durham, NC (US); Filip Kielar, Malá Morávka (CZ)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/564,081

(22) Filed: Aug. 1, 2012

(65) Prior Publication Data

US 2013/0035311 A1    Feb. 7, 2013

Related U.S. Application Data

(60) Provisional application No. 61/515,144, filed on Aug. 4, 2011.

(51) Int. Cl.
*A01N 55/08*    (2006.01)
*A61K 31/69*    (2006.01)

(52) U.S. Cl.
USPC .............................. 514/64; 558/288; 546/13

(58) Field of Classification Search
None
See application file for complete search history.

(56) References Cited

U.S. PATENT DOCUMENTS

| 2009/0253161 A1 | 10/2009 | Franz et al. |
| 2010/0004204 A1 | 1/2010 | Franz et al. |
| 2011/0184333 A1 | 7/2011 | Franz et al. |

OTHER PUBLICATIONS

Kielar F et al. Prochelator BHAPI protects cells against paraquat-induced damage by ROS-triggered iron chelation. Metallomics. The Royal Society of Chemistry 2012. DOI: 10.1039/c2mt20069d. 11 pp.

*Primary Examiner* — Brandon Fetterolf
*Assistant Examiner* — Jean Cornet
(74) *Attorney, Agent, or Firm* — Myers Bigel Sibley & Sajovec, P.A.

(57) ABSTRACT

The present invention provides compounds of Formula I along with compositions containing the same and methods of use thereof in treating oxidative stress.

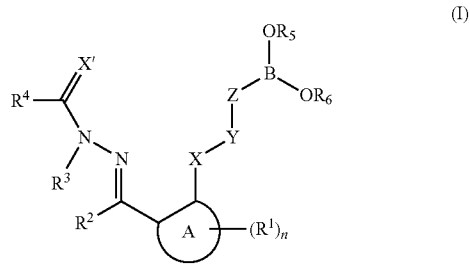

(I)

22 Claims, 2 Drawing Sheets

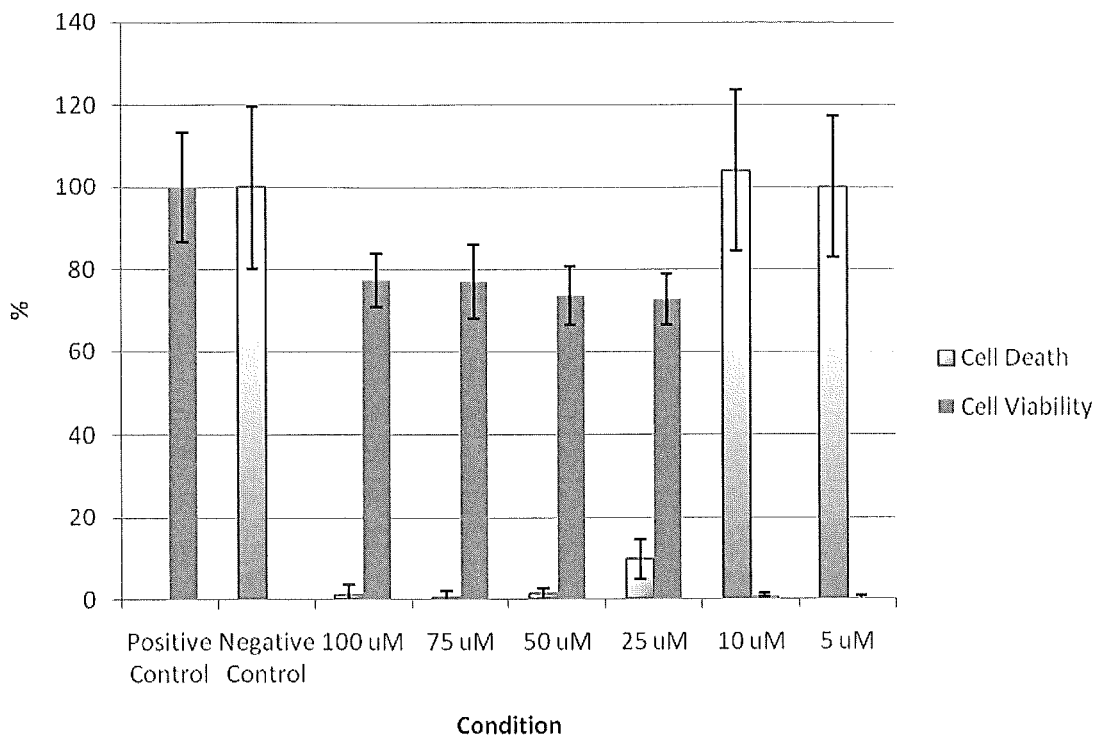
Figure 1. Protection of ARPE cells with B-HAPI from $H_2O_2$.
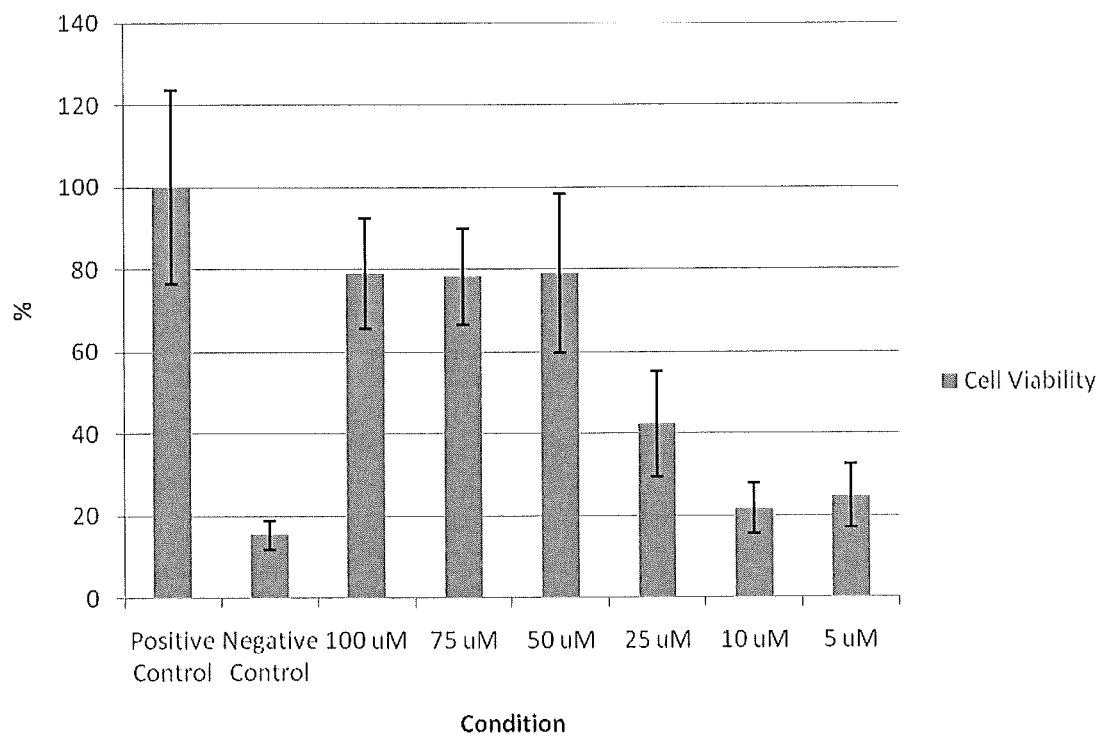
Figure 2. Protection of SHSY-5Y cells with B-HAPI from $H_2O_2$.

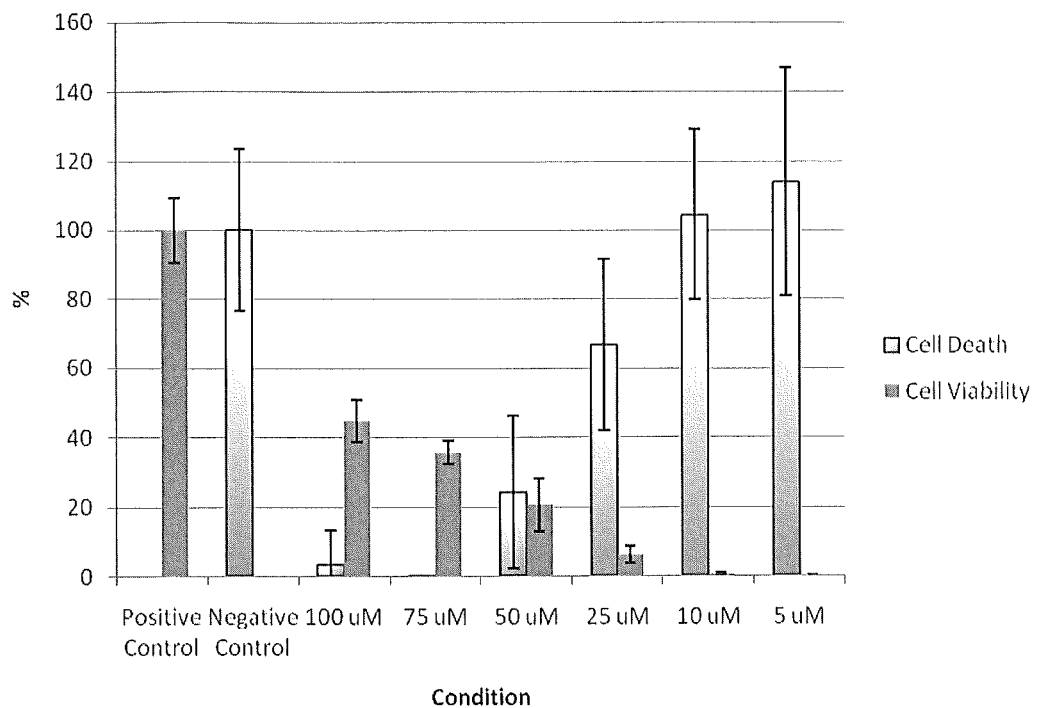
Figure 3. Protection of ARPE cells with B-HAPI from paraquat.
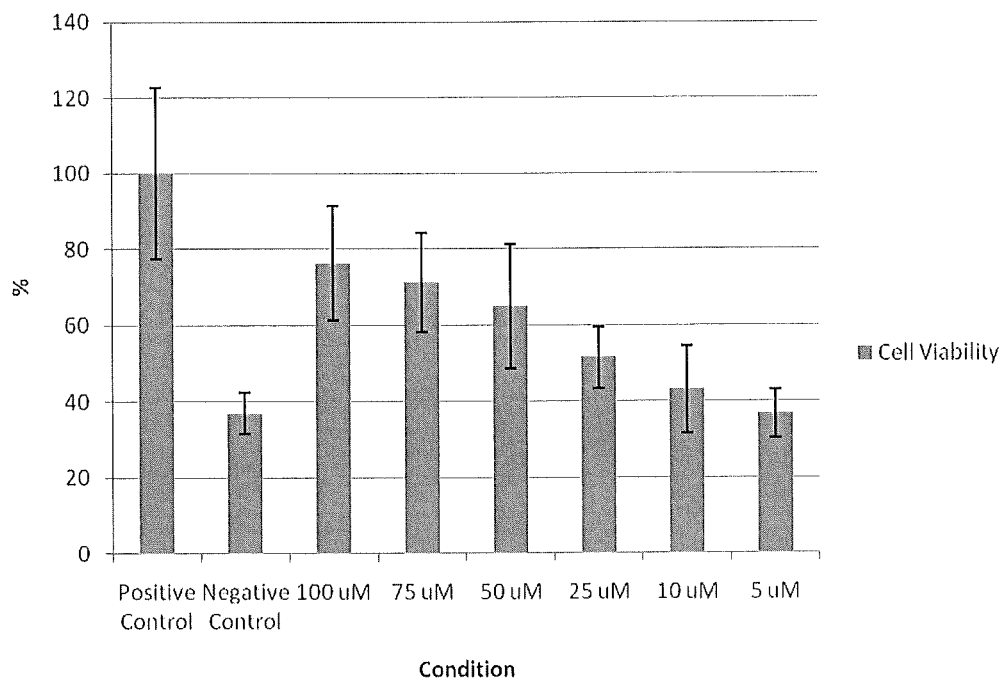
Figure 4. Protection of ARPE cells with B-HAPI from paraquat.

US 8,551,976 B2

PROCHELATORS FOR INHIBITING METAL-PROMOTED OXIDATIVE STRESS

RELATED APPLICATIONS

This application claims the benefit of U.S. Provisional Patent Application Ser. No. 61/515,144, filed Aug. 4, 2012, the disclosure of which is incorporated by reference herein in its entirety.

STATEMENT OF GOVERNMENT SUPPORT

This invention was made with Government support under contract number RO1-GM084176 awarded by the National Institutes of Health. The Government has certain rights in the invention.

FIELD OF THE INVENTION

The present invention concerns aroylhydrazone iron chelators, pharmaceutical formulations containing the same and methods of use thereof.

BACKGROUND OF THE INVENTION

Neurodegenerative diseases such as Parkinson's and Alzheimer's show signs of increased oxidative stress that result when reactive oxygen species (ROS) overwhelm a cell's inherent antioxidant mechanisms. Markers of oxidative stress include lipid peroxidation, DNA base hydroxylation, and protein modification, all of which are attributed to the highly reactive hydroxyl radical, OH·. While many potential antioxidant therapies use radical scavengers in attempts to mitigate cellular damage, such strategies do not inhibit formation of these harmful radicals. See generally Franz and Charkoudian, US Patent Application Publication No. 2010/0004204 (Jan. 7, 2010).

SUMMARY OF THE INVENTION

A first aspect of the present invention is a compound of Formula I (sometimes referred to as "active compounds" herein):

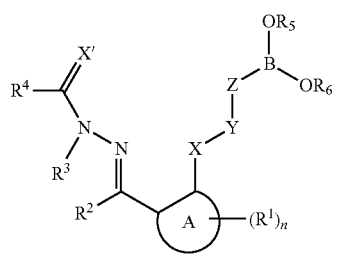

(I)

wherein:
X is O, —OC(=O)O—, or —NHC(=O)O— (e.g., where N is bonded to A and O is bonded to Y);
Y is $CH_2$ or —CHCH—;
Z is aryl or arylaryl;
X' is O or S;
A is aryl;
n is an integer from 1 to 4;
each $R^1$ is independently selected from the group consisting of: alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;
$R^2$ and $R^3$ are each independently H, alkyl, or hydroxy;
$R^4$ is alkyl, cycloalkyl, heterocyclo, or aryl;
$R^5$ and $R^6$ are independently selected H, alkyl, or haloalkyl, or together form an alkylene bridge, which alkylene bridge may be unsubstituted or substituted from 1 to 4 times with alkyl, halo, a fused cycloalkyl or a fused aryl ring;
and pharmaceutically acceptable salts or prodrugs thereof.

A second aspect of the invention is a pharmaceutical formulation comprising an active compound as described herein in a pharmaceutically acceptable carrier.

A further aspect of the present invention is a method of treating a subject afflicted with an oxidative stress disease, comprising administering said subject a therapeutically effective amount of an active compound as described herein.

A further aspect of the present invention is a method of iron chelation therapy in a subject in need thereof, comprising administering said subject a therapeutically effective amount of an active compound as described herein.

A further aspect of the invention is the use of an active compound as described herein for the treatment of oxidative stress in a subject in need thereof or for the preparation of a medicament for treating oxidative stress in a subject in need thereof.

In some embodiments of the foregoing, the subject is afflicted with a neurodegenerative disease such as Parkinson's disease, cardiovascular disease, cancer, an iron overload disorder, hemochromatosis, β-thalassemia or Friedrich's ataxia.

The present invention is explained in greater detail in the drawings herein and the specification set forth below.

BRIEF DESCRIPTION OF THE DRAWINGS

FIG. 1. Plot of cell viability and cell death for protection of ARPE cells with B-HAPI from 200 μM $H_2O_2$.

FIG. 2. Plot of cell viability for protection of SHSY-5Y cells with B-HAPI from 200 μM $H_2O_2$.

FIG. 3. Plot of cell viability and cell death for protection of ARPE cells with B-HAPI from 10 mM paraquat over 48 hours.

FIG. 4. Plot of cell viability for protection of ARPE cells with B-HAPI from 5 mM paraquat over 24 hours.

DETAILED DESCRIPTION OF PREFERRED EMBODIMENTS

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, isopropyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, isopropyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkylene bridge" as used herein refers to a straight or branched chain hydrocarbon bridging species containing from 1 to 10 carbon atoms. Representative examples include, but are not limited to, C1-C5 bridges such as —(CH$_2$)$_n$— where n is 1 or 2 to 3, 4 or 5. The term "alkylene bridge" is intended to include both substituted and unsubstituted unless otherwise indicated and may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. Bicyclic and tricyclic ring systems are also included. These rings may be optionally substituted with additional substituents as described herein such as halo or loweralkyl. The term "cycloalkyl" is generic and intended to include heterocyclic groups as discussed below unless specified otherwise.

"Heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. In some embodiments aryl contains a "hetero" atom and is also a "heterocyclo" group as described above. The term "aryl" is intended to include both substituted and unsubstituted aryl unless otherwise indicated and these groups may be substituted with the same groups as set forth in connection with alkyl and loweralkyl above. More specifically, "aryl" groups as used herein may be substituted 1, 2, 3, or 4 or more times with independently selected halo (e.g., haloaryl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Arylaryl" refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Any "aryl" may be used, substituted or unsubstituted, and optionally containing a heteroatom, as described above. Typical arylaryl groups include, but are not limited to, biphenyl, triphenyl, phenyl-naphthyl, binaphthyl, biphenyl-naphthyl, and the like, which may be substituted or unsubstituted as described in connection with aryl above. Where the number of carbon atoms in an arylaryl group are specified, the numbers refer to the carbon atoms comprising each parent aromatic ring. For example, ($C_{5}$-$C_{14}$) arylaryl is an arylaryl group in which each aromatic ring comprises from 5 to 14 carbons, e.g., biphenyl, triphenyl, binaphthyl, phenylnaphthyl, etc. Preferably, each parent aromatic ring system of an arylaryl group is independently a ($C_{5}$-$C_{14}$) aromatic, more preferably a ($C_{5}$-$C_{10}$) aromatic. In some embodiments, preferred are arylaryl groups in which all of the parent aromatic ring systems are identical, e.g., biphenyl, triphenyl, binaphthyl, trinaphthyl, etc. See, e.g., U.S. Pat. No. 6,750,199.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Diol" as used herein refers to a chemical compound containing two hydroxyl groups.

"Nitro" as used herein refers to an —$NO_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)$NR_aR_b$ radical, where $R_a$ and $R_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —$S(O)_2NR_aR_b$ radical, where $R_a$ and $R_b$ are any suitable substituent such as H, alkyl, cycloalkyl, alkenyl, alkynyl or aryl.

"Urea" as used herein alone or as part of another group refers to an —$N(R_c)C(O)NR_aR_b$ radical, where $R_a$, $R_b$ and $R_c$, are any suitable substituent such as H, alkyl, cycloalkyl, alkenyl, alkynyl or aryl.

"Alkoxyacylamino" as used herein alone or as part of another group refers to an —$N(R_a)C(O)OR_b$ radical, where $R_a$, $R_b$ are any suitable substituent such as H, alkyl, cycloalkyl, alkenyl, alkynyl or aryl.

"Aminoacyloxy" as used herein alone or as part of another group refers to an —$OC(O)NR_aR_b$ radical, where $R_a$ and $R_b$ are any suitable substituent such as H, alkyl, cycloalkyl, alkenyl, alkynyl or aryl.

"Treat" as used herein refers to any type of treatment that imparts a benefit to a patient afflicted with a disease or disorder, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Treat" as used herein refers to any type of treatment that imparts a benefit to a patient afflicted with a disease or disorder, including improvement in the condition of the patient (e.g., in one or more symptoms), delay in the progression of the disease, etc.

"Oxidative stress disease" as used herein may be any disease that can be treated by the compounds and methods of the invention (and including disorders attributable to iron or copper induced oxidative stress) including but not limited to cancer, neurodegenerative disease, inflammatory disease, cardiovascular disease, diabetes, and iron chelation therapy subjects in general, etc.

"Iron chelation therapy" as used herein may be carried out on subjects in need of such treatment for any reason, including but not limited to subjects afflicted with cancer, neurodegenerative disease, cardiovascular disease, iron-overload disorders (e.g., from iron poisoning, hemochromatosis (iron overload disease), and transfusional hemosiderosis in Cooley's Anemia, sickle cell anemia, aplastic anemia and forms of leukemia), β-thalassemia, and Friedrich's ataxia. See, e.g., U.S. Pat. Nos. 6,989,397; 5,663,201; and 4,613,616.

"Cancer" as used herein may be any type of cancer, including but not limited to lung cancer, colon cancer, colorectal cancer, breast cancer, prostate cancer, ovarian cancer, liver cancer, leukemia, lymphoma, etc.

"Neurodegenerative disease" is a disease in which cells of the brain and/or spinal cord are lost. Known neurodegenerative diseases in which copper metabolism has been implicated include Alzheimer's disease, amyotrophic lateral sclerosis (ALS), Parkinson's disease, and human prion disease such as Creutzfeldt-Jakob disease. See, e.g., Gaggelli et al., Chemistry Reviews 106:1995-2044 (2006); Waggoner et al., Neurobiology of Disease 6:221-230 (1999); Mercer, Trends in Molecular Medicine, 7(2):64-69 (2001).

Other diseases, conditions or traumas known to involve copper include Wilson disease, Menkes disease, Pick's disease, and aceruloplasminemia. In addition, toxicity associated with copper and hydrogen peroxide include ischemic insults such as stroke, and seizures. See, e.g., Horning et al., Brain Research 852:56-61 (2000); Madsen et al. Annu. Rev. Neurosci. 30:317-337 (2007).

"Expanded polyglutamine repeat diseases" (or "polyglutamine repeat diseases") include, but are not limited to, Huntington's disease, dentatorubral pallidoluysian atrophy, spinobulbar muscular atrophy, and spinocerebellar ataxia types 1, 2, 3, 6 and 7. See, e.g., U.S. Pat. No. 6,632,616 to Burke et al.

"Pharmaceutically acceptable" as used herein means that the compound or composition is suitable for administration to a subject to achieve the treatments described herein, without unduly deleterious side effects in light of the severity of the disease and necessity of the treatment.

Active compounds of the present invention may optionally be administered in conjunction with other compounds useful in iron chelation therapy (e.g., in the treatment of neurodegenerative diseases). The other compounds may optionally be administered concurrently. As used herein, the word "concurrently" means sufficiently close in time to produce a combined effect (that is, concurrently may be simultaneously, or it may be two or more events occurring within a short time period before or after each other).

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

1. Active Compounds.

As noted above, the present invention provides compounds of Formula I:

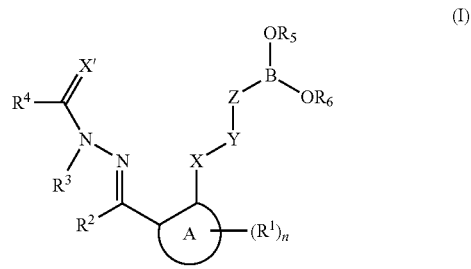

wherein:

X is O, —OC(=O)O—, or —NHC(=O)O— (e.g., where N is bonded to A and O is bonded to Y);

Y is $CH_2$ or —CHCH—;

Z is aryl or arylaryl;

X' is O or S;

A is aryl n is an integer from 1 to 4;

each $R^1$ is independently selected from the group consisting of: alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

$R^2$ and $R^3$ are each independently H, alkyl, or hydroxy;

$R^4$ is alkyl, cycloalkyl, heterocyclo, or aryl;

$R^5$ and $R^6$ are independently selected H, alkyl, or haloalkyl, or together form an alkylene bridge, which alkylene bridge may be unsubstituted or substituted from 1 to 4 times with alkyl, halo, a fused cycloalkyl or a fused aryl ring;

and pharmaceutically acceptable salts or prodrugs thereof.

In some embodiments of the foregoing, X is O.

In some embodiments of the foregoing, the compound has a structure of Formula Ia, Ib or Ic:

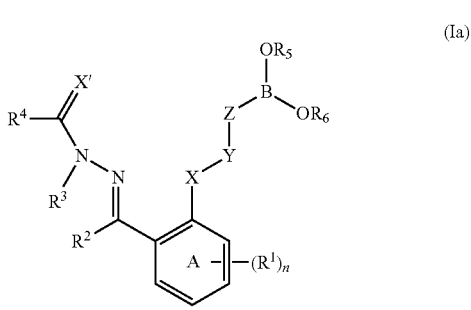

-continued

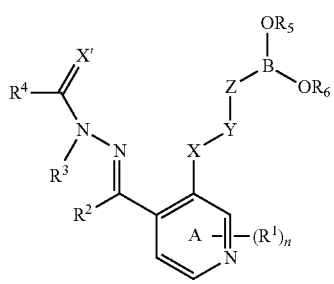
(Ib)

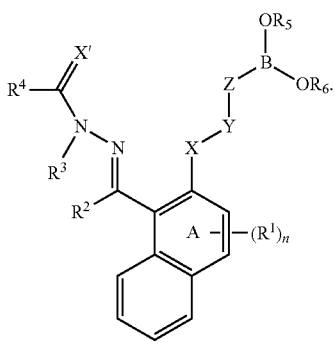
(Ic)

In some embodiments of the foregoing, —X—Y—Z— together form a group selected from the group consisting of:

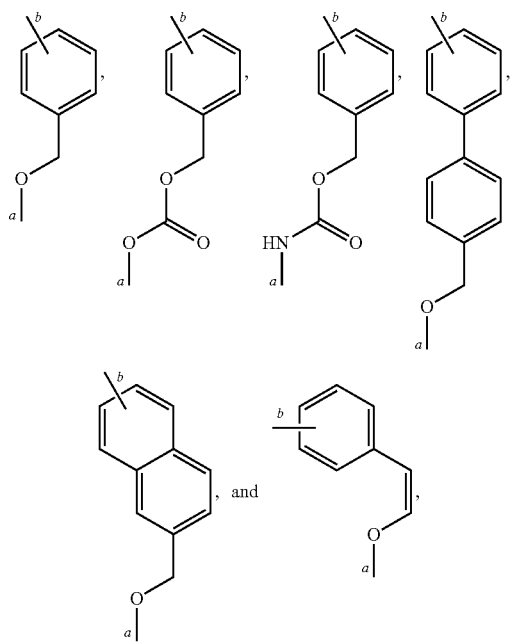

where bond a is a covalent bond to ring A and bond b is a covalent bond (e.g., in ortho or para orientation) to B.

In some embodiments of the foregoing, $R^4$ is aryl, such as phenyl, pyridinyl, thiophenyl, furanyl, pyrrolyl, pyrazolyl, imidazolyl, oxazolyl, thiazolyl, pyrimidinyl, and pyridinyl, which aryl may be unsubstituted or substituted, for example from 1 to 3 times with independently selected substituents from the group consisting of alkyl, hydroxyl, alkoxy, amino, alkyoamino, dialkylamino, and halo.

In some embodiments of the foregoing, $R^4$ is selected from the group consisting of:

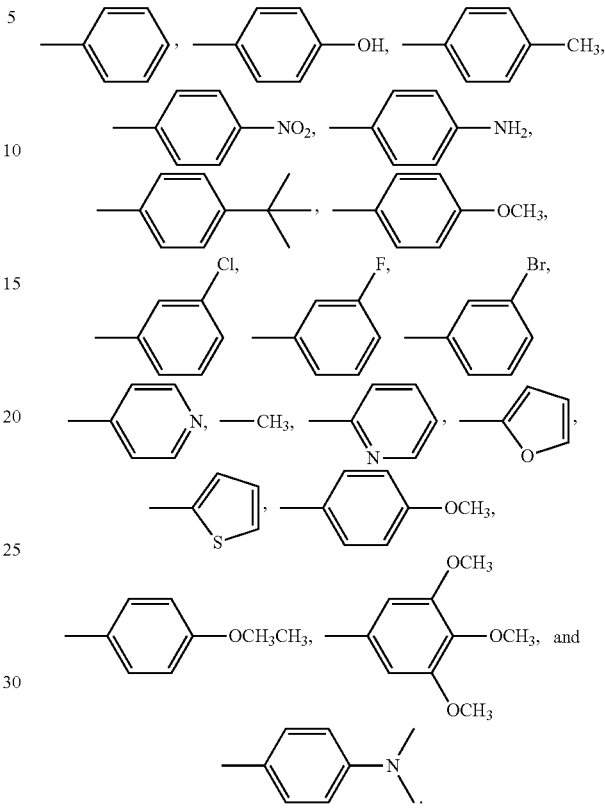

In some embodiments of the foregoing, $R^5$ and $R^6$ are independently selected H, alkyl, or haloalkyl.

In some embodiments of the foregoing, $R^5$ and $R^6$ together form an alkylene bridge, which alkylene bridge may be unsubstituted or substituted from 1 to 4 times with alkyl, halo, a fused cycloalkyl or a fused aryl ring.

In some embodiments of the foregoing, $R^5$ and $R^6$ together form a C2 or C3 alkylene bridge having a bicyclic cycloalkyl substituted thereon (e.g., a C5 to C12 bicyclic cycloalkyl), which alkylene bridge and/or bicyclic cycloalkyl may be unsubstituted or substituted from 1 to 4 times with alkyl or halo.

In some embodiments of the foregoing:
$R^5$ and $R^6$ are both H;
$R^5$ and $R^6$ are both $CH_3$; or
$R^5$ and $R^6$ together form a bridge selected from the group consisting of

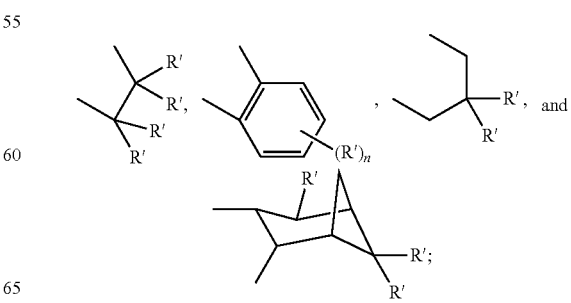

where n is 0, 1, 2, 3 or 4 and each R' is independently, H, alkyl or halo.

Example compounds of the present invention include, but are not limited to:

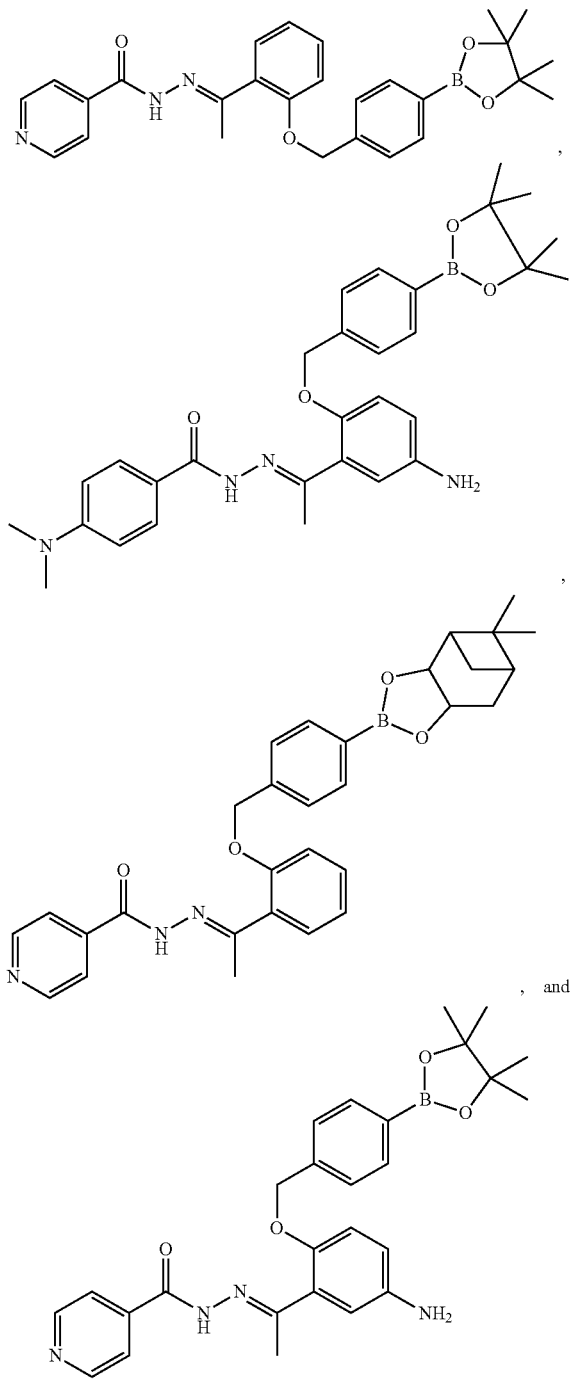

and pharmaceutically acceptable salts thereof.

Compounds of the present invention can be made in accordance with known techniques or variations thereof that will be apparent to those skilled in the art given known techniques and the present disclosure. See U.S. Pat. Nos. 6,989,397 and 6,329,378; see also D. Richardson and P. Ponka, *J. Lab Clin Med.* 131, 306-314 (1998); T. Simunek et al., *J. Mol. Cell. Cardiol.* 39, 345-354 (2005); D. Kalinowski and D. Richardson, *Pharmacol. Rev.* 57, 547-583 (2005); M. Yang et al., *J. Am. Chem. Soc.* 126, 15392-15393 (2004); E. Miller et al., *J. Am. Chem. Soc* 127, 16652-16659 (2005).

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Pharmaceutically acceptable prodrugs as used herein refers to those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

2. Pharmaceutical Formulations.

The active compounds described above may be formulated for administration in a pharmaceutical carrier in accordance with known techniques. See, e.g., Remington, *The Science And Practice of Pharmacy* (9 th Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art. As a general proposition, a dosage from about 0.1 or 1.0 to about 250 or 500 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 200 mg/kg may be employed for oral administration. Typically, a dosage from about 1 mg/kg to 100 mg/kg may be employed for intramuscular injection. The duration of the treatment is usually once per day for a period of two to three weeks or until the condition is essentially controlled. Lower doses given less frequently can be used prophylactically to prevent or reduce the incidence of recurrence of the disease.

4. Combination Treatments.

In another embodiment, it is envisioned to use an active compound of the invention in combination with other therapeutic modalities, in like manner as described in U.S. Pat. No. 6,946,441 to Long et al. Thus, in addition to the therapies described above, one may also provide to the patient more additional therapies for the treatment of neurodegenerative disease. The particular therapy will depend upon the disease being treated. Examples of such therapies for Parkinson's disease include but are not limited to levodopa (L-DOPA; with or without carbidopa), dopamine agonists (such as apomorphine, bromocriptine, pergolide, pramipexole, ropinirole, etc.) anticholinergics such as atropine, scopolamine, glycopyrrolate, trihexyphenidyl, benztropine mesylate, procyclidine, etc.), monoamine oxidase (MAO-B) inhibitors such as selegiline, COMT inhibitors (preferably taken with levodopa) such as entacapone and tolcapone and other medications such as amantadine, etc., and including pharmaceutically acceptable salts and prodrugs thereof, and combinations of any of the foregoing. See, e.g., U.S. Pat. No. 6,833,478.

The additional active agent may be administered separately from the active agents of the present invention, or the two combined together in a single composition.

Compositions containing an active agent of the invention in combination with an additional active or therapeutic agent such as an antiparkinson's agent are prepared in like manner as described above and techniques that will be apparent to those skilled in the art. Such compositions may be prepared in any suitable unit dosage form including injectable forms and oral dosage forms such as tablets and capsules, as described above.

The present invention is explained in greater detail in the following non-limiting Examples.

EXPERIMENTAL

General. Unless otherwise noted, chemicals were purchased commercially (Sigma Aldrich) and used without further purification. NMR spectra were collected on a Varian Inova 400 and a Varian Unity 500 spectrometers with chemical shifts reported in ppm and J values in Hz. Liquid chromatography/mass spectrometry (LC/MS) was performed using an Agilent 1100 Series apparatus with an LC/MSD trap and a Daly conversion dynode detector. A Varian Polaris C18 (150× 1.0 mm) column was used and peaks were detected by UV absorption at 280 nm. A linear gradient from 15% B in A to 50% B in A was run from 2 to 12 min followed with second linear part to 95% B in A between 12 and 16 min. The total run time was 22 min. A is water/2% MeCN/0.1% formic acid and B is MeCN/2% water/0.1% formic acid.

Synthesis of 1-(2-(4-(4,4,5,5-tetramethyl-1,3,2-dioxaborolan-2-yl)benzyloxy)phenyl)ethanone

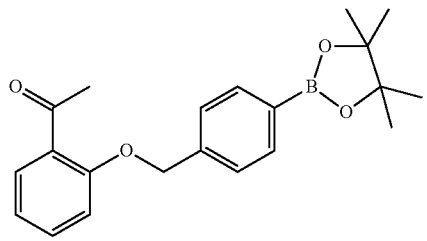 [SMILES: CC(=O)c1ccccc1OCc1ccc(B2OC(C)(C)C(C)(C)O2)cc1]

A mixture of 2-hydroxy-acetophenone (0.3 g, 2.2 mmol), 4-bromomethylphenylboronic acid pinacol ester (0.8 g, 2.7 mmol) and potassium carbonate (0.3 g, 2.2 mmol) in DMF (5 ml) was heated up to 110° C. for 24 h. The reaction mixture composition was determined by TLC and 4-bromomethylphenylboronic acid pinacol ester (0.3 g, 1.0 mmol) was added. The reaction mixture was heated to 110° C. for additional 24 h. The solvent was removed in vacuo. The crude product was purified by column chromatography on silica ($CH_2Cl_2$ to 4% MeOH) to give the desired product as an oil (0.51 g, 1.4 mmol, 64%). $\delta_H$ ($CDCl_3$, 400 MHz): 1.24 (12H, s, $CH_3$), 2.59 (3H, s, $COCH_3$), 6.98 (1H, dd, $^3J$=9.2, $^4J$=1.6), 7.00 (1H, dd, $^3J$=8.4, $^4J$=0.8), 7.41 (1H, dd, $^4J$=4), 7.43 (2H, d, $^3J$=8.4), 7.74 (1H, dd, $^3J$=7.6, $^4J$=1.6), 7.83 (2H, d). $\delta_C$ ($CDCl_3$, 125 MHz): 24.91 ($CH_3$), 32.15 ($COCH_3$), 70.62 ($C_{qart}$), 83.95 ($CH_2$), 112.80 ($C_{Ar}$), 120.93 ($C_{Ar}$), 126.78 ($C_{Ar}$), 128.72 ($C_{Ar}$), 130.52 ($C_{Ar}$), 133.62 ($C_{Ar}$), 135.16 ($C_{Ar}$), 139.23 ($C_{Ar}$), 158.00 ($C_{Ar}$), 199.93 (CO). m/z (ES+) 391.1 $[M+K]^+$ calc for $C_{21}H_{25}BKO_4$ 391.2.

N'-(1-(2-(4-(4,4,5,5-tetramethyl-1,3,2-dioxaborolan-2-yl)benzyloxy)phenyl)ethylidene)isonitotinohdrazide (B-HAPI)

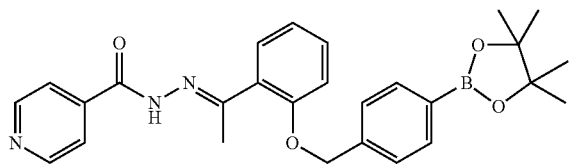 [SMILES: C/C(=N\NC(=O)c1ccncc1)c1ccccc1OCc1ccc(B2OC(C)(C)C(C)(C)O2)cc1]

A mixture of 1-(2-(4-(4,4,5,5-tetramethyl-1,3,2-dioxaborolan-2-yl)benzyloxy)phenyl)ethanone (240 mg, 0.68 mmol) and isonicotinichydrazide (93 mg, 0.68 mmol) was stirred under reflux in a mixture of toluene and DMF (9:1; 50 ml) for 32 h. The apparatus was equipped with a Dean-Stark adaptor for water removal from the reaction mixture. The solvent was removed in vacuo. The crude product was purified by column chromatography on silica and isolated as a yellowish oil (170 mg, 0.36 mmol, 53%). The product was isolated as a mixture of the E/Z isomers of the hydrazone double bond. $\delta_H$(DMSO, 400 MHz): 1.27 (24H, s, CH$_3$), 2.28 (3H, s, COCH$_3$), 2.32 (3H, s, COCH$_3$), 5.19 (4H, s, CH$_2$), 6.98-7.08 (2H, m), 7.15-7.28 (4H, m), 7.38-7.49 (8H, m), 7.62 (2H, d, $^3$J=8.8), 7.70 (2H, d, $^3$J=7.6), 7.78 (2H, d, $^3$J=4.8), 8.61 (2H, d, 3J=5.2), 8.74 (2H, d, $^3$J=4). m/z (ES+) 494.2 [M+Na]$^+$ calc for C$_{27}$H$_{30}$BN$_3$NaO$_4$ 494.2.

Hydrogen Peroxide Oxidation. A 40 mM stock solution of B-HAPI in DMSO was prepared. The reaction mixture (2 mM B-HAPI) was prepared by mixing 50l of the B-HAPI stock solution with 450 µl of water and 450 µl of DMSO. The reaction was initiated by addition of 50 µl of concentrated (30%) H$_2$O$_2$ solution. The reaction mixture was incubated at room temperature for 1 h and analyzed by LC-MS. Formation of the chelator (HAPI) and the intermediate of the self-immolative deprotection reaction was observed (data not shown).

Cell Culture. All cell culture agents, including minimal essential medium (MEM), Dulbecco's modified eagle medium (DMEM), F12 Ham's nutrient mix (F12), fetal bovine serum (FBS), pencillin-streptomycin (pen-strep), L-glutamine, and trypsin-EDTA were purchased from Gibco. LDH Release Assay Kit was obtained from Roche Diagnostics and CellTiter-Blue Cell Viability Assay from Promega. Cell viability assays were performed on a Perkin Elmer Victor31420 plate reader. Live cell images were taken on ZeissAxio Observer widefield fluorescence microscope under 20× magnification using a Plan Neofluar objective lens. A filter set for red part of visible spectra (FS43HE: BP550/25, FT570, BP605/70) was used to collect fluorescence emission data.

The spontaneously immortalized human retinal pigment epithelial cell line ARPE-19 was purchased from American Type Culture Collection. The cells were grown in 1:1 DMEM and F12 medium with FBS (10%), pen-strep (1%), and glutamine (1%). Cells were cultured until confluent in 24-well Falcon plates. The The dopaminergic human neuroblastoma cell line SHSY-5Y was purchased from American Type Culture Collection. The cells were grown in 1:1 MEME and F12 medium with FBS (10%), pen-strep (1%), and non essential amino acids (1%). Cells were cultured until confluent in 24-well Falcon plates.

Cell Experiments. Stock solution of B-HAPI (5 mM) was prepared in 50 mM sodium hydroxide and stored at −20° C. The stock solution was diluted to 100 M in MEM and pH was adjusted to the range 7.4-7.8 with dilute HCl. Solutions of lower concentration were prepared by further dilution in MEM.

Protection from Hydrogen Peroxide (ARPE, SHSY-5Y). The growth media was removed, cells were washed three times with MEM and treated with appropriate B-HAPI concentration (0 µM, 5 µM, 10 µM, 25 µM, 50 M, 75 µM and 100 µM). Cells were incubated for 5 h and H$_2$O$_2$ was added to achieve final concentration of 200 µM. The cells were incubated for further 19 h and the viability was determined using CellTiter-Blue Cell Viability Assay (cell life assay) and/or LDH release assay kit (cell death assay). The conditions compared in each experiment were: positive control (cell treated only with MEM), negative control (cells treated with MEM containing H$_2$O$_2$) and cells treated with a range of B-HAPI concentrations and H$_2$O$_2$. Each condition was run in triplicate and variability was determined as the standard deviation of the results (FIG. 1, FIG. 2).

Protection from Paraquat (ARPE). The growth media was removed, cells were washed three times with MEM and treated with appropriate B-HAPI concentration (0 µM, 5 µM, 10 µM, 25 µM, 50 M, 75 M and 100 µM). Paraquat was added to achieve final concentration of 5 mM (24 h experiment) or 10 mM (48 h experiment). The cells were incubated for further 24 or 48 h and the viability was determined using CellTiter-Blue Cell Viability Assay and/or LDH release assay kit (FIG. 3, FIG. 4).

Cell Imaging. Phase contrast and fluorescence (propidium iodide) imaging was performed with cells treated with 10 mMparaquat for 48 h. Propidium iodide stains nuclei of cells with compromised integrity of their cell walls, thus providing visualization for dying cells. Cells were grown to confluence on a 12 well plate with a glass window and treated as described above for the paraquat experiment. Propidiumidodide (7.5 µM) was added to the media after 48 h and allowed to incubate for 30 min. The media was drain, cells were washed three times with PBS and fresh MEM was added for the imaging experiment (data not shown).

REFERENCES

1. Quin, C.; Robertson, L.; McQuaker, S. J.; Price, N. C.; Brand, M. D.; Hartley, R. C., Caged Mitochondrial Uncouplers that are Released in Response to Hydrogen Peroxide. *Tetrahedron* 2010, 66, 2384-2389.
2. Jourden, J. L. M.; Cohen, S. M., Hydrogen Peroxide Activated Matrix Metalloproteinase Inhibitors: A Prodrug Approach. *Angew. Chem. Int. Ed.* 2010, 49, 6795-6797.
3. Weinstein, R.; Baran, P. S.; Shabat, D., Activity-Linked Labeling of Enzymes by Self-Immolative Polymers. *Bioconjugate Chem.* 2009, 20, 1783-1791.
4. Avital-Shmilovici, M.; Shabat, D., Dendritic Chain Reaction: Responsive Release of Hydrogen Peroxide upon Generation and Enzymatic Oxidation of Methanol. *Bioorg. Med. Chem.* 2010, 18, 3643-3647.

The foregoing is illustrative of the present invention, and is not to be construed as limiting thereof. The invention is defined by the following claims, with equivalents of the claims to be included therein.

What is claimed is:
1. A compound of Formula I:

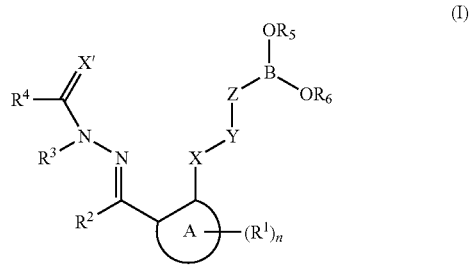

wherein:
X is O, —C(=O)O—, or —NHC(=O)O—;
Y is CH$_2$ or —CHCH—;
Z is aryl or arylaryl;
X' is O or S;
A is aryl
n is an integer from 1 to 4;
each R$^1$ is independently selected from the group consisting of: alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

$R^2$ and $R^3$ are each independently H, alkyl, or hydroxy;

$R^4$ is alkyl, cycloalkyl, heterocyclo, or aryl;

$R^5$ and $R^6$ are independently selected H, alkyl, or haloalkyl, or together form an alkylene bridge, which alkylene bridge may be unsubstituted or substituted from 1 to 4 times with alkyl, halo, a fused cycloalkyl or a fused aryl ring;

and pharmaceutically acceptable salts or prodrugs thereof.

2. The compound of claim 1, wherein X' is O.

3. The compound of claim 1, wherein said compound has a structure of Formula Ia, Ib or Ic:

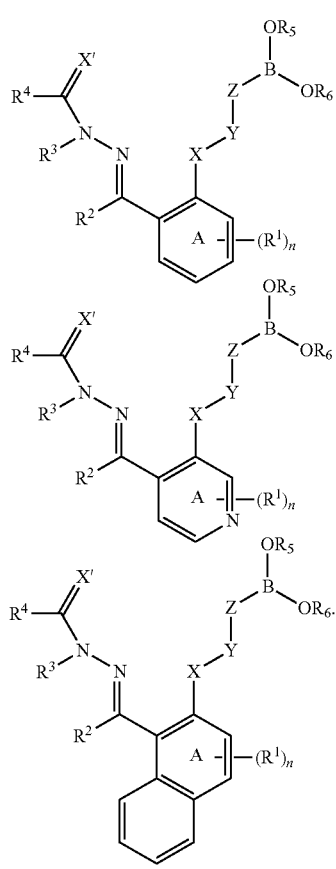

4. The compound of claim 1, wherein —X—Y—Z— together form a group selected from the group consisting of:

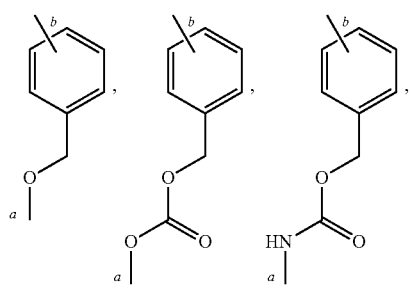

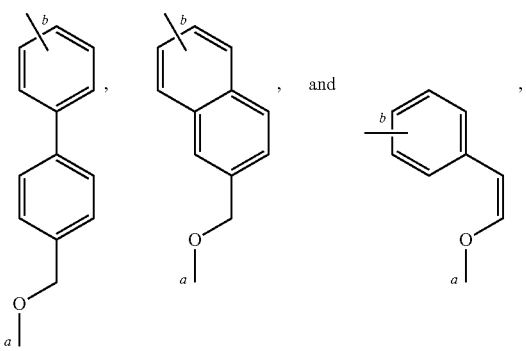

where bond a is a covalent bond to ring A and bond b is a covalent bond to B.

5. The compound of claim 1, wherein $R^4$ is aryl, which aryl is selected from the group consisting of phenyl, pyridinyl, thiophenyl, furanyl, pyrrolyl, pyrazolyl, imidazolyl, oxazolyl, thiazolyl, pyrimidinyl, and pyridinyl, which aryl may be unsubstituted or substutituted from 1 to 3 times with independently selected substituents from the group consisting of alkyl, hydroxyl, alkoxy, amino, alkyoamino, dialkylamino, and halo.

6. The compound of claim 5, wherein $R^4$ is selected from the group consisting of:

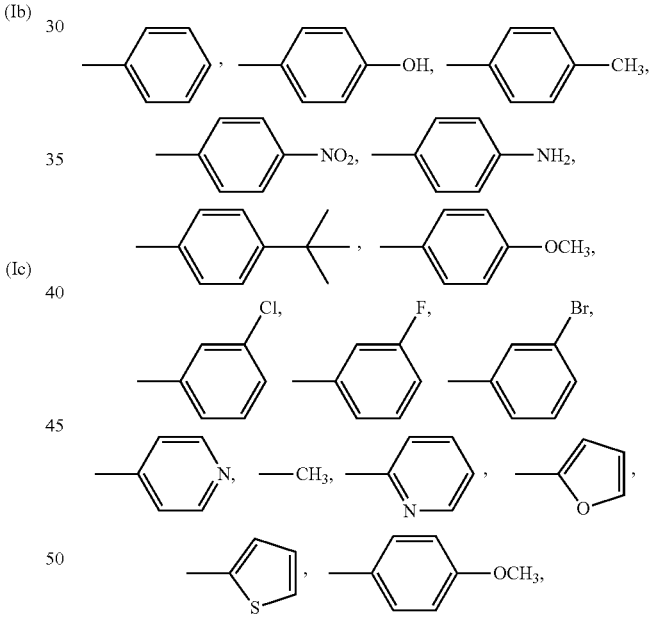

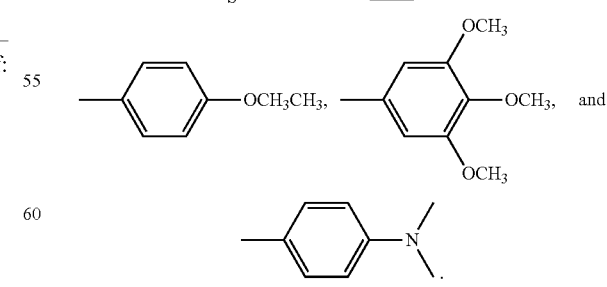

7. A compound of claim 1, wherein $R^5$ and $R^6$ are both H;

$R^5$ and $R^6$ are both $CH_3$; or $R^5$ and $R^6$ together form a bridge selected from the group consisting of:

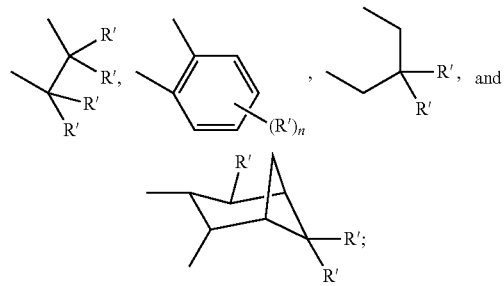

where n is 0, 1, 2, 3 or 4 and each R' is independently, H, alkyl or halo.

8. The compound of claim 1, wherein said compound has a structure of Formula Ia:

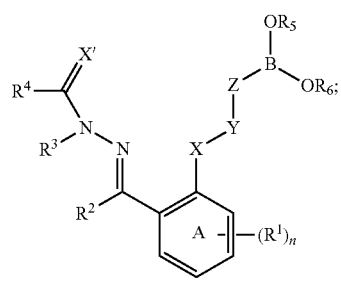

(Ia)

—X—Y—Z— together form a group:

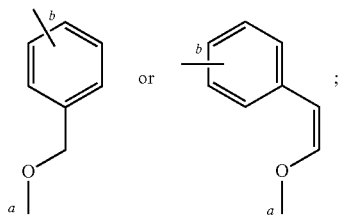

where bond a is a covalent bond to ring A and bond b is a covalent bond to B;

$R^4$ is selected from the group consisting of:

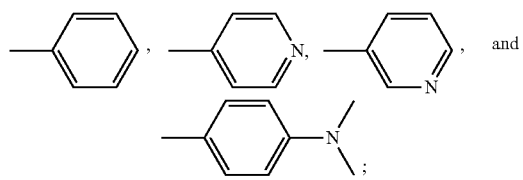

X' is O;

$R^5$ and $R^6$ are both H; $R^5$ and $R^6$ are both $CH_3$; or $R^5$ and $R^6$ together form a bridge selected from the group consisting of

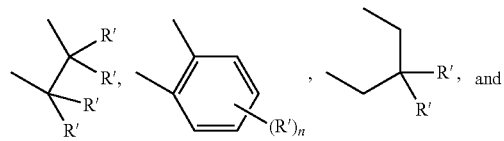

-continued

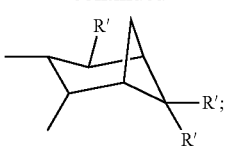

where n is 0, 1, 2, 3 or 4 and each R' is independently, H, alkyl or halo.

9. A compound of claim 1 having the structure:

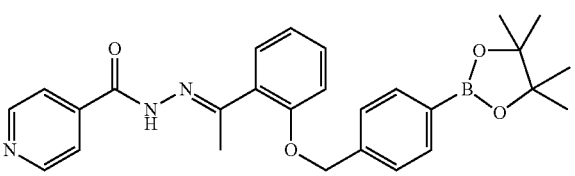 [SMILES: C/C(=N\NC(=O)c1ccncc1)c1ccccc1OCc1ccc(B2OC(C)(C)C(C)(C)O2)cc1]

or a pharmaceutically acceptable salt thereof.

10. A compound of claim 1 having the structure:

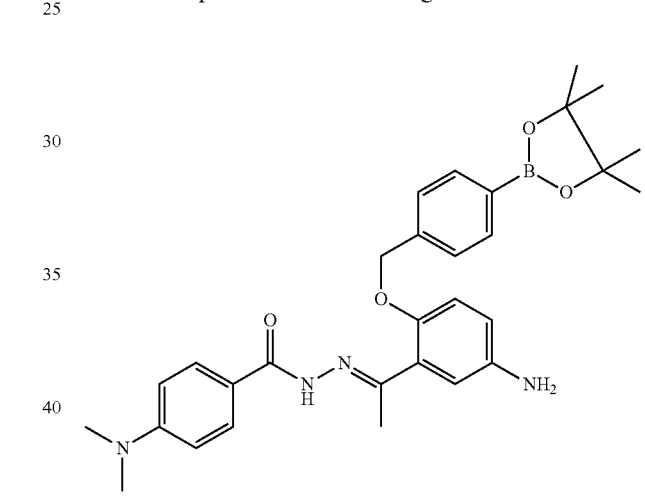

or a pharmaceutically acceptable salt thereof.

11. A compound of claim 1 having the structure:

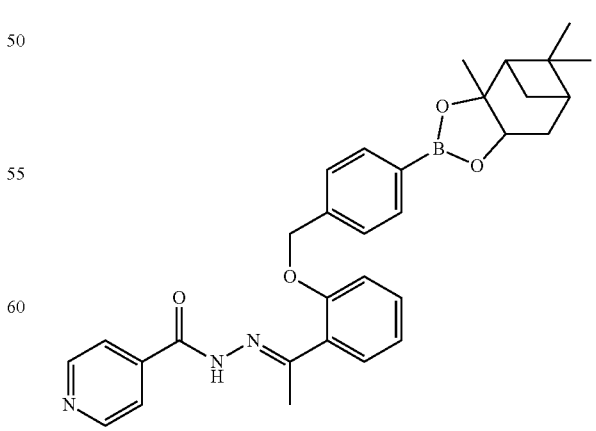

or a pharmaceutically acceptable salt thereof.

12. A compound of claim 1 having the structure:

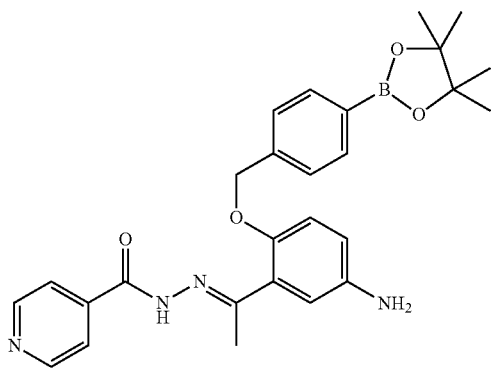 [SMILES: C/C(=N\NC(=O)c1ccncc1)c1cc(N)ccc1OCc1ccc(B2OC(C)(C)C(C)(C)O2)cc1]

or a pharmaceutically acceptable salt thereof.

13. A pharmaceutical formulation comprising a compound of claim 1 in a pharmaceutically acceptable carrier.

14. A method of treating a subject afflicted with an oxidative stress disease, comprising administering said subject a therapeutically effective amount of a compound of claim 1.

15. A method of iron chelation therapy in a subject in need thereof, comprising administering said subject a therapeutically effective amount of a compound of claim 1.

16. The method of claim 15, wherein said subject is afflicted with amyotrophic lateral sclerosis and Alzheimer's disease.

17. The method of claim 15, wherein said subject is afflicted with Parkinson's disease.

18. The method of claim 15, wherein said subject is afflicted with cardiovascular disease.

19. The method of claim 15, wherein said subject is afflicted with leukemia.

20. The method of claim 15, wherein said subject is afflicted with an iron overload disorder.

21. The method of claim 15, wherein said subject is afflicted with hemochromatosis.

22. The method of claim 15, wherein said subject is afflicted with β-thalassemia or Friedrich's ataxia.

* * * * *

UNITED STATES PATENT AND TRADEMARK OFFICE
CERTIFICATE OF CORRECTION

Page 1 of 2

PATENT NO. : 8,551,976 B2
APPLICATION NO. : 13/564081
DATED : October 8, 2013
INVENTOR(S) : Franz et al.

It is certified that error appears in the above-identified patent and that said Letters Patent is hereby corrected as shown below:

In the Specification

Column 11, Lines 28-43:
Correct the compound below:

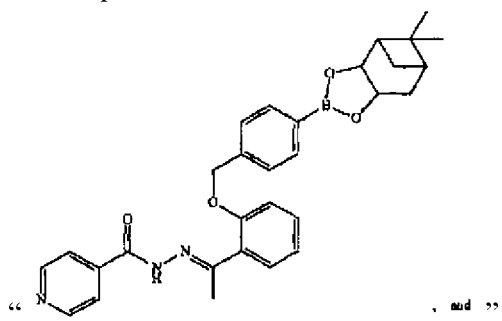

", and "

...to read

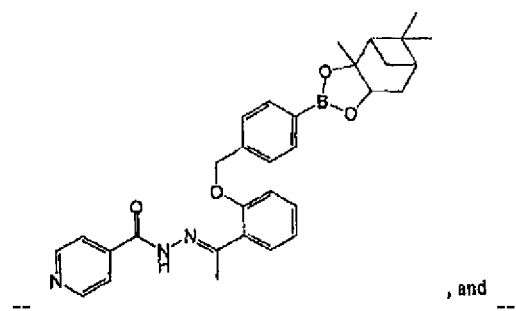

, and

Column 17, Line 17: "prepared by mixing 501 of the B-HAPI"
to read -- prepared by mixing 50 µl of the B-HAPI --

Column 17, Line 52: "diluted to 100 M in MEM"
to read -- diluted to 100 µM in MEM --
Column 17, Line 58: "25 µM, 50 M, 75 µM and 100"

Signed and Sealed this
Twenty-fourth Day of June, 2014

Michelle K. Lee
*Deputy Director of the United States Patent and Trademark Office*

CERTIFICATE OF CORRECTION (continued)
U.S. Pat. No. 8,551,976 B2 to read -- 25 μM, 50 μM, 75 μM and 100 --

Column 18, Line 6: "10 μM, 25 μM, 50 M, 75 M and 100 μM)."
        to read -- 10 μM, 25 μM, 50 μM, 75 μM and 100 μM). --